United States Patent [19]

Blaha et al.

[11] 4,026,293

[45] May 31, 1977

[54] PHOTOCOAGULATOR

[75] Inventors: Erich Blaha, Wasseralfingen; Walter Lang; Ortwin Mueller, both of Koenigsbronn, all of Germany

[73] Assignee: Carl Zeiss-Stiftung, Oberkochen, Germany

[22] Filed: May 16, 1975

[21] Appl. No.: 577,991

[30] Foreign Application Priority Data

May 21, 1974 Germany .................... 7417688[U]

[52] U.S. Cl. ............................. 128/303.1; 128/396
[51] Int. Cl.² ........................................... A61F 9/00
[58] Field of Search ............... 128/303.1, 395, 396, 128/397, 398

[56] References Cited

UNITED STATES PATENTS

| | | | |
|---|---|---|---|
| 1,559,062 | 10/1925 | Anderson | 128/397 |
| 1,806,318 | 5/1931 | Tillyer | 128/397 X |
| 2,930,379 | 3/1960 | Dopp et al. | 128/396 |
| 3,084,694 | 4/1963 | Kavanagh et al. | 128/303.1 X |
| 3,096,767 | 7/1963 | Gresser et al. | 128/395 |
| 3,796,220 | 3/1974 | Bredemeier | 128/303.1 |

FOREIGN PATENTS OR APPLICATIONS 1,206,861   9/1970   United Kingdom ............ 128/303.1

*Primary Examiner*—Channing L. Pace
*Attorney, Agent, or Firm*—Stonebraker, Shepard & Stephens

[57] ABSTRACT

A photocoagulator using a gas discharge lamp and a mirror for forming a double image of the luminous plasma region of the lamp in a photocoagulation area adjusted for size by interchangeable field stops is improved for easier adjustability when field stop sizes are changed. A manually operable screw ring moves the lamp axially relative to the mirror to adjust the separation of one image from the other relative to the size of the field stop, and the side of the field stop facing toward the coagulation area is illuminated for brightening the environment of the coagulation area for easier observation.

16 Claims, 5 Drawing Figures

PHOTOCOAGULATOR

BACKGROUND OF THE INVENTION

Photocoagulators are generally well known in opthalmology for producing a "weld" between the retina and the choroid tissue. The retina is coagulated locally by means of light energy applied to a selected coagulation area. Such instruments use a gas discharge lamp, and preferably a high-pressure xenon arc lamp, to supply the light energy. The instruments have an optical system along a light output path for imaging a luminous plasma region of the lamp on the patient's eye via intermediate images, and a concave mirror behind the lamp reflects light from the luminous plasma region out along the output path to form another image of the luminous plasma region reflected from the mirror. The two images of the plasma region have to be positioned in diametrically opposite relation at the perimeter of the field stop to achieve optimum illumination.

Photocoagulators have interchangeable field stops preferably mounted on a "rekoss" disk so that different sized field stops can be positioned on the output path. Each time the field stop size is changed, the instrument must be adjusted for proper location of the direct and reflected images of the plasma region at the edges of the field stop. In prior art photocoagulators, this required projection of an intermediate image onto a nearby wall and adjustment of the instrument with a wrench in a relatively cumbersome and slow procedure.

The invention involves recognition of the problems of adjusting prior art photocoagulators and realization of a way that adjustment can be made simpler, faster, and more convenient. The invention aims at simplicity, efficiency, reliability, and ease of adjustment in an improved photocoagulator.

SUMMARY OF THE INVENTION

The invention applies to a photocoagulator having a gas discharge lamp, optical means in a light output path for forming an image of a luminous plasma region of the lamp, a mirror arranged for reflecting light from the luminous plasma region through the optical means to form another image of the luminous plasma region, and a plurality of interchangeable field stops arranged in the region of the output path for adjusting the size of the coagulation area. The inventive improvement includes manually operable means for moving the lamp axially relative to the mirror to adjust the separation of one image from the other image relative to a selected field stop, and means for illuminating the side of the field stop facing toward the coagulation area to provide additional illumination around the coagulation area to facilitate observation of the operating field while the instrument is in use.

The axial adjustment for the lamp is preferably a rotatable screw ring for moving the lamp relative to a housing supporting the mirror, and a mark and scale are preferably arranged between the housing and the screw ring for indicating the position of the lamp. The additional illumination for the side of the field stop facing the coagulation area is preferably provided by light derived from the lamp and conducted through a light pipe to a reflecting element that directs the light onto the field stop.

In one preferred embodiment of the invention, the mirror and field stops are mounted on an outer housing, an intermediate housing is movable relative to the outer housing, and the lamp is mounted in an inner housing coupled to the intermediate housing by a universal joint allowing tilt adjustment of the housing in two predetermined planes. The universal joint is preferably a portion of a sphere and a socket shaped to receive the sphere portion.

These improvements allow fast and convenient adjustment of the instrument whenever field stop sizes are changed, and also allow easier observation through better illumination of the region around the coagulation area so that the instrument is much less cumbersome and much more efficient.

DETAILED DESCRIPTION OF THE INVENTION

Figure 1:
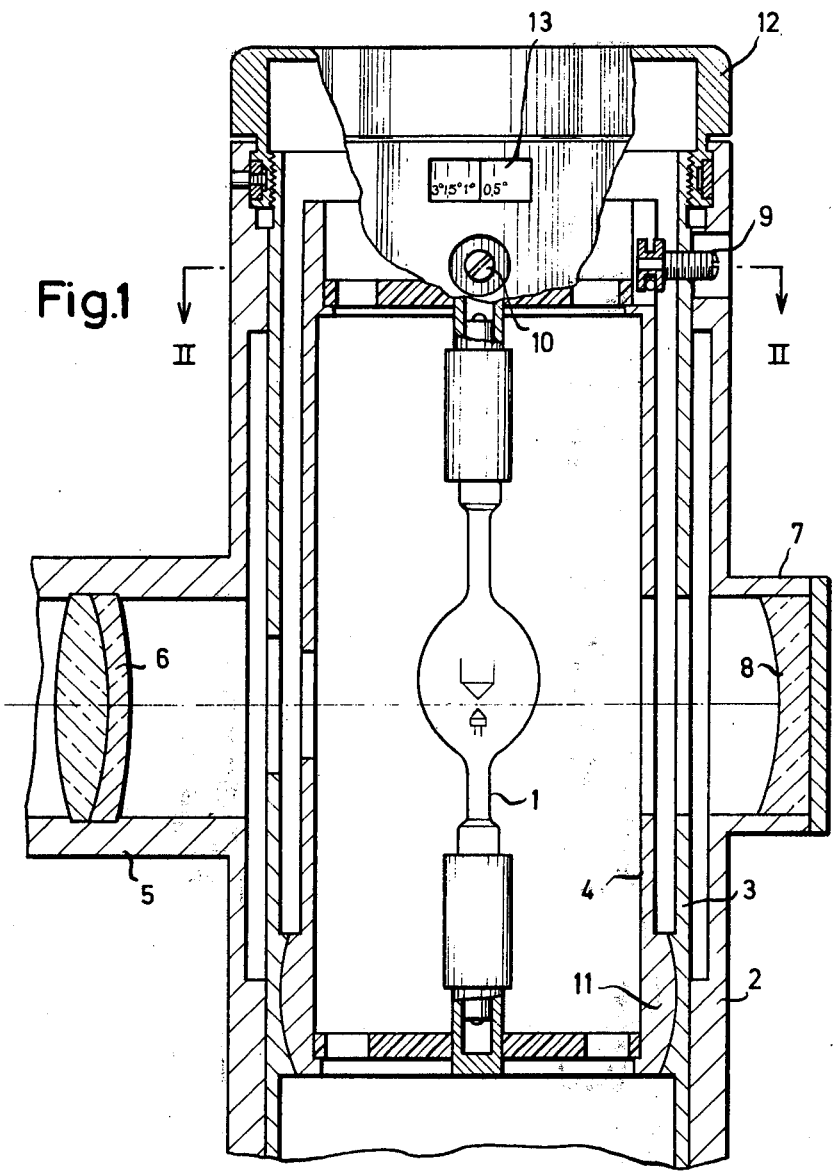
FIG. 1 is a partially cross-sectioned, fragmentary elevational view of a preferred embodiment of the inventive photocoagulator.
Figure 2:
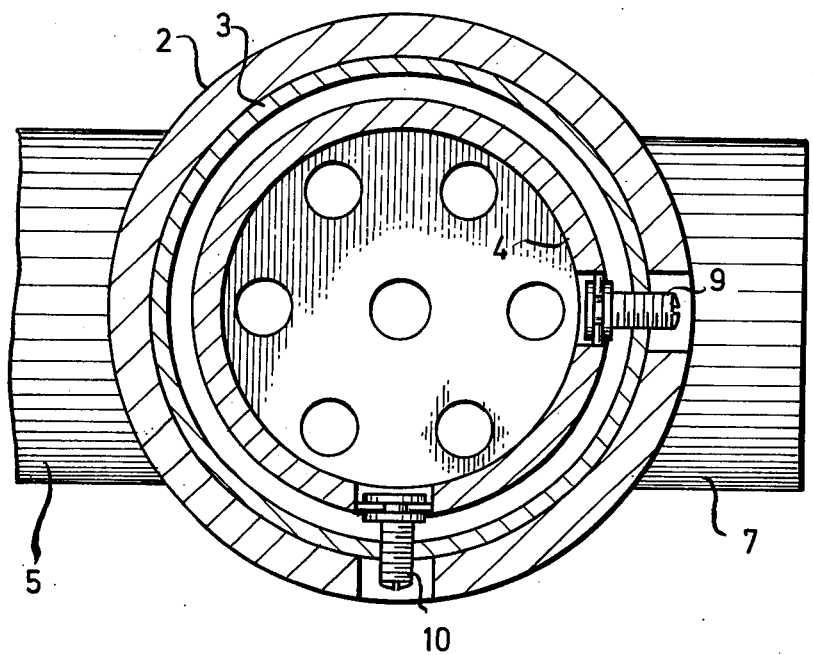
FIG. 2 is a cross section of the photocoagulator of FIG. 1 taken along the line II—II thereof.

FIG. 1 best shows a preferred embodiment of the invention for adjusting a high-pressure xenon arc lamp 1 in a photocoagulator. The housing for the instrument is generally formed of three metallic tubes or housing parts including an outer tube 2, an intermediate tube 3, and an inner tube 4. The outer tube 2 includes an integral optical guide 5 surrounding an output path for the light from the xenon arc lamp 1 directed toward the patient's eye. Optical guide 5 includes a first lens group 6 forming a portion of an optical system for the output from the lamp 1.

Opposite the output path through sleeve 5 is a concave mirror 8 mounted in a lateral projection 7 in the outer housing 2. The mirror 8 reflects light from the luminous plasma region of the lamp 1 back toward the lamp 1 and out the output path through the sleeve 5 and the lens system 6. This allows formation of both a direct and a reflected image of the plasma region of the lamp 1 in the output of the instrument.

The intermediate housing 3 is slidable in the direction of the axial extent of the lamp 1 within the outer housing 2, and a screw ring 12 is threaded to the intermediate housing 3 and turns in a track that is fixed relative to the outer housing 2 for axially positioning the intermediate housing 3 relative to the outer housing 2. A dial 13 in the outer housing 2 has numerical indications of the size of the coagulation field, and the screw ring 12 has a mark that is positioned along the dial 13 to set the correct distance between the direct and reflected images of the luminous plasma of the lamp 1 for each size of field stop in the instrument output. The dial 13 can also be placed on the screw ring 12 with a mark or pointer on the outer housing 2 to accomplish the same general purpose.

The inner housing 4 is preferably tiltable within the intermediate housing 3, and a preferred arrangement for this uses a portion of a ball or sphere 11 on the inner housing 4 movably positioned within a cup or socket shaped in the intermediate housing 3 so that the socket fits the spherical portion 11 and allows tilting movement of the inner housing 4. Such tilt adjustment is accomplished by a pair of screws 9 and 10 threaded through the intermediate housing 3 and coupled to the inner housing 4 for adjusting the tilt of the inner housing 4 in a pair of predetermined coordinates or planes that are preferably perpendicular to each other as illustrated.

Figure 4:
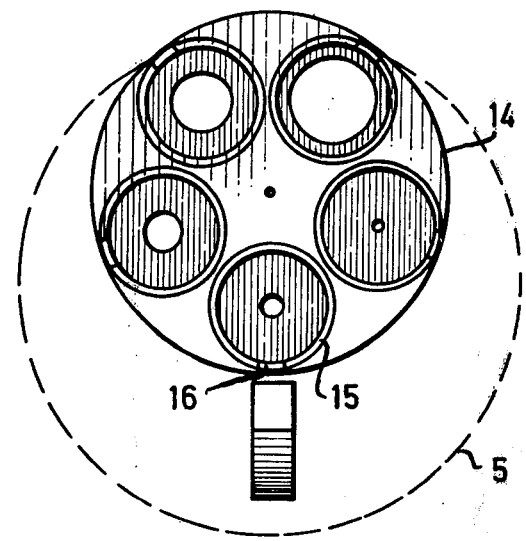
FIG. 4 is a front elevational view of a "rekoss" disk bearing different sized field stops to adjust the coagulation area.

The interchangeable field stops 15 are preferably mounted on a "rekoss" disk 14 as best shown in FIG. 4. The field stops 15 can be selectively positioned in the output of the optical guide 5 conducting light from the lamp toward the patient's eye, and the field stops 15 are preferably arranged at an intermediate-image position along the optical guide 5. The field stops 15 are interchanged by rotating the disk 14.

Figure 5:
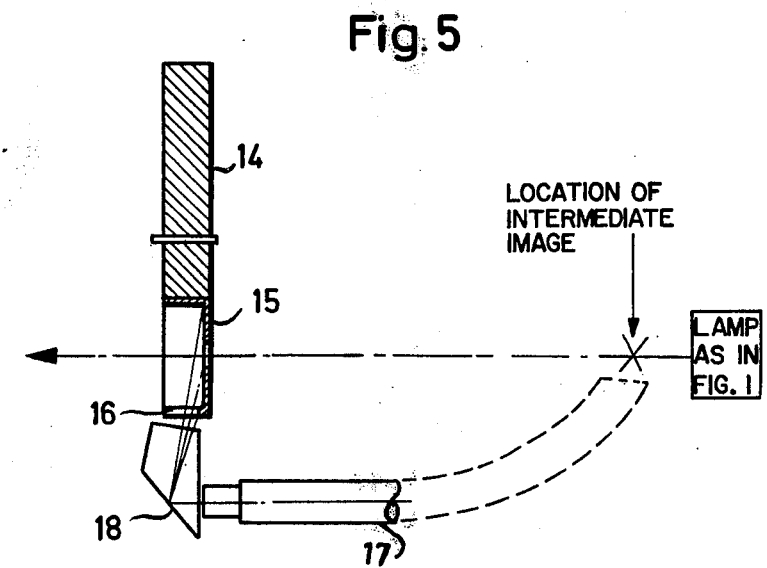
FIG. 5 is a partially cross-sectional view through the field stop disk of FIG. 4 showing a preferred way of illuminating the field stops.

As best shown in FIG. 5, each of the field stops 15 is preferably shaped as a hollow cup open toward the patient's eye with radiation passing through the field stop 15 in the direction of the arrow as illustrated. A notch or radiation opening 16 is formed in each of the field stops 15 to allow illumination of the side of the field stop facing toward the photocoagulation area. This is preferably done by light derived from the xenon lamp as received by a light pipe 17 at a convenient region along the optical guide where an intermediate image of the luminous plasma is formed. Pipe 17 leads from such an intermediate image region to a prism 18 so that light from the arc plasma not required for the coagulation is used for brightening the field stop 15. A mirror can also be used in place of prism 18, and the face of the field stop 15 illuminated by light transmitted through the light pipe 17 is preferably metallically reflecting or alternatively provided with a white coating for diffusing illumination. The illumination of the side of the field stop facing the patient then provides additional illumination directed toward the patient around the area of the coagulation to aid in observing the adjustment and operation of the instrument.

Figure 3:
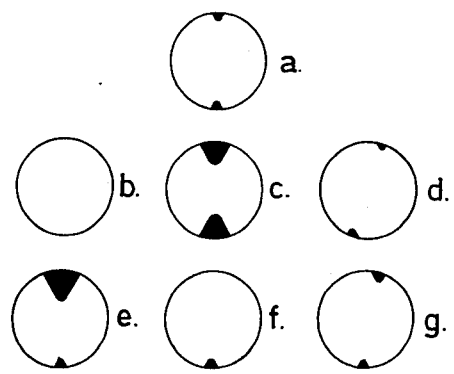
FIG. 3 is a schematic view of seven possible image relationships of the plasma region of the lamp relative to a field stop aperture, to illustrate the image adjustment performed by the inventive photocoagulator.

The circle a—g of FIG. 3 illustrate different types of possible illumination of a field stop aperture as revealed when the light passing through the field stop is projected onto a nearby wall to check for proper adjustment of the instrument. A direct image of the luminous plasma region of the xenon lamp is positioned adjacent one rim of the field stop, and the image of the luminous plasma light reflected from the instrument's mirror is positioned in a diametrically opposite relation near the rim of the field stop. The optimum illumination is shown in circle a of FIG. 3 where the direct image and the reflected image of the luminous plasma of the lamp are located just inside the periphery of the field stop circle and diametrically opposed at the top and bottom of the field stop.

If the field stop is then enlarged from the adjustment of circle a of FIG. 3, the direct and reflected images will extend too far into the interior of the field stop opening as shown in circle c so that readjustment by turning the screw ring 12 is required. If the field stop is diminished from the adjustment of circle a the opposite effect of circle b is produced and also requires adjustment of the screw ring 12. Both axial adjustment through the screw ring 12, and tilting adjustment through the set screws 9 and 10 are available to remedy the misadjustments of circles d—g of FIG. 3, and the dial 13 especially facilitates any reqired axial adjustment of the xenon lamp.

In operation, the instrument is adjusted by using both the screw ring 12 and adjusting screws 9 and 10 to set the direct and reflected luminous plasma images relative to a field stop as shown in circle a of FIG. 3 for using the instrument. The adjusting and positioning of the instrument is facilated by the easier observation made possible by the extra illumination of the patient's side of the field stop to brighten the region around the coagulation area. Then if a field stop is changed by rotating the disk 14, a quick readjustment of the instrument can be made by turning the screw ring 12 to set the dial 13 to the new field stop size. The adjustment can also be checked by projecting an intermediate image on a nearby wall and making any necessary tilt or axial adjustments to achieve the optimum positioning of the direct and reflected images relative to any selected field stop as shown in circle a of FIG. 3. The improved illumination of the region around the coagulation area and the faster and simpler adjustment make the instrument much more efficient and reduce the time required for operations with the instrument.

Those skilled in the art will appreciate the different adjustment mechanisms and coupling devices and the different ways the concepts of the invention can be applied to specific instruments to accomplish the intended impovements.

What is claimed is:

1. A photocoagulator comprising
   a. a gas discharge lamp elongated along a lamp axis and having a light output path along an optical axis approximately perpendicular to said lamp axis,
   b. optical means in said light output path for forming an image of light from said lamp at a distance along said optical axis from said lamp,
   c. a mirror arranged on said optical axis on the opposite side of said lamp from said optical means, for reflecting light from said lamp along said optical axis and through said optical means to form a second image at a distance,
   d. a plurality of interchangeable field stops,
   e. means for holding said field stops in position so that any one of said field stops may be brought to a position aligned with said optical axis at said distance from said lamp,
   f. manually operable means for moving said lamp axially along said lamp axis to adjust said first mentioned image relative to said second image and to the selected field stop aligned with said optical axis, and
   g. means for illuminating the side of the selected field stop which is remote from said lamp.

2. The photocoagulator of claim 1 wherein said mirror is arranged in a housing and said axial movement producing means includes a rotatable screw ring for moving said lamp relative to said housing.

3. The photocoagulator of claim 2 including a mark and a scale arranged on said housing and said screw ring for indicating the position of said lamp.

4. The photocoagulator of claim 1 including means for deriving light for said illuminating means from said lamp.

5. The photocoagulator of claim 4 including a light pipe arranged for receiving light from said lamp, and a reflecting element arranged for directing light from said light pipe onto said selected field stop.

6. The photocoagulator of claim 1 including an outer housing, an intermediate housing, and an inner housing, and wherein said mirror and said field stops are mounted in said outer housing, said intermediate housing is movable relative to said outer housing in the direction of the axial extent of said lamp, said lamp is mounted in said inner housing, and a universal joint means supports said inner housing in said intermediate housing for allowing said inner housing to tilt relative to said intermediate housing in two predetermined planes.

7. The photocoagulator of claim 6 wherein said universal joint means includes a portion of a sphere and a socket shaped to receive said sphere portion.

8. The photocoagulator of claim 6 including a pair of adjusting screws coupled between said inner housing and said intermediate housing for adjusting said tilt of said inner housing.

9. The photocoagulator of claim 6 wherein said axial movement producing means includes a rotatable screw ring between said outer housing and said intermediate housing.

10. The photocoagulator of claim 9 including a mark and a scale arranged on said housing and said screw ring for indicating the position of said lamp.

11. The photocoagulator of claim 10 including means for deriving light for said illuminating means from said lamp.

12. The photocoagulator of claim 11 including a light pipe arranged for receiving light from said lamp, and a reflecting element arranged for directing light from said light pipe onto said selected field stop.

13. The photocoagulator of claim 12 including a pair of adjusting screws coupled between said inner housing and said intermediate housing for adjusting said tilt of said inner housing.

14. The photocoagulator of claim 12 wherein said universal joint includes a portion of a sphere and a socket shaped to receive said sphere portion.

15. The photocoagulator of claim 6 including means for deriving light for said illuminating means from said lamp.

16. The photocoagulator of claim 15 including a light pipe arranged for receiving light from said lamp, and a reflecting element for directing light from said light pipe onto said selected field stop.

* * * * *